(12) United States Patent
Salvati et al.

(10) Patent No.: US 7,649,005 B2
(45) Date of Patent: Jan. 19, 2010

(54) SUBSTITUTED BENZYLAMINOALKYLENE HETEROCYCLES

(75) Inventors: Patricia Salvati, Bresso (IT); Carla Caccia, Bresso (IT); Piero Melloni, Bresso (IT); Alessandra Restivo, Bresso (IT); Cibele Sabido David, Bresso (IT); Stefania Vallese, Baranzate Di Bollate (IT)

(73) Assignee: Newron Pharmaceuticals S.p.A., Bresso (IT)

( * ) Notice: Subject to any disclaimer, the term of this patent is extended or adjusted under 35 U.S.C. 154(b) by 472 days.

(21) Appl. No.: 10/575,627

(22) PCT Filed: Oct. 5, 2004

(86) PCT No.: PCT/EP2004/011104

§ 371 (c)(1),
(2), (4) Date: May 15, 2006

(87) PCT Pub. No.: WO2005/040138

PCT Pub. Date: May 6, 2005

(65) Prior Publication Data

US 2007/0135496 A1   Jun. 14, 2007

(30) Foreign Application Priority Data

Oct. 15, 2003 (EP) .................................. 03023342

(51) Int. Cl.
*A61K 31/44* (2006.01)
*C07D 213/02* (2006.01)

(52) U.S. Cl. ................ 514/357; 514/365; 514/374; 514/378; 514/394; 514/400; 514/438; 514/461; 546/329; 548/198; 548/215; 548/240; 548/335.1; 549/13; 549/356; 549/440; 549/491

(58) Field of Classification Search ............... None
See application file for complete search history.

(56) References Cited

U.S. PATENT DOCUMENTS

| 4,145,439 A | 3/1979 | Kraus et al. |
| 4,623,662 A | 11/1986 | De Vries |
| 5,318,988 A | 6/1994 | Schohe-Loop et al. |
| 6,303,819 B1 | 10/2001 | Pevarello et al. |

FOREIGN PATENT DOCUMENTS

| DE | 298 507 | 2/1992 |
| EP | 0 534 246 | 3/1993 |
| FR | 2 181 559 | 12/1973 |
| WO | WO 94/26738 | 11/1994 |
| WO | WO 97/05102 | 2/1997 |
| WO | WO 97/05111 | 2/1997 |
| WO | WO 99/35125 | 7/1999 |
| WO | WO 01/12604 | 2/2001 |

OTHER PUBLICATIONS

Bowlby M.R. et al.:, "Epilepsy drug review: patent activity from 1999 to 2002" Expert Opinion on Therapeutic Patents, vol. 13, No. 7, Jul. 1, 2003, pp. 979-1001, XP002270128.

*Primary Examiner*—Zinna N Davis
(74) *Attorney, Agent, or Firm*—Young & Thompson

(57) ABSTRACT

This invention is related to compounds of general formula (I) wherein X is oxygen or sulphur or a $NR^7$ group; $R^1$ is $C_3$-$C_8$ alkyl, or $C_1$-$C_8$ alkyl substituted by phenoxy or phenyl, both phenoxy or phenyl being optionally substituted by one or more fluoro, chloro, trifluoromethyl, $C_1$-$C_6$ alkyl, hydroxyl, $C_1$-$C_6$ alkoxy; $R^2$, $R^3$ are independently hydrogen, $C_1$-$C_6$ alkyl, halogen, trifluoromethyl, hydroxy or $C_1$-$C_6$ alkoxy; $R^4$ is hydrogen, $C_1$-$C_8$ alkyl; $R^5$, $R^6$ are independently hydrogen, $C_1$-$C_3$ alkyl, optionally substituted by hydroxy or phenyl; $R^7$ is hydrogen or straight or branched $C_1$-$C_3$ alkyl; Het is a five to seven membered, saturated or unsaturated heteromonocyclic or an eight to ten membered, saturated or unsaturated heterobicyclic group, containing one or more heteroatoms chosen independently from nitrogen, oxygen and sulphur, said mono- or bicyclic groups being optionally substituted by $C_1$-$C_6$ alkyl, halogen, hydroxyl or $C_1$-$C_6$ alkoxy; and the pharmaceutically acceptable salts or prodrug thereof, that are active as sodium and/or calcium channel modulators and/or as selective MAO-B inhibitors and therefore useful in preventing, alleviating and curing a wide range of pathologies, including, but not limited to, neurological, psychiatric, cardiovascular, inflammatory, ophthalmic, urologic, metabolic and gastrointestinal diseases, where the above mechanisms have been described as playing a pathological role.

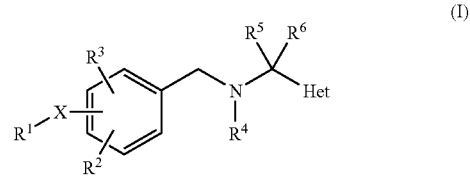

(I)

6 Claims, No Drawings

SUBSTITUTED BENZYLAMINOALKYLENE HETEROCYCLES

This invention is related to compounds of general formula I

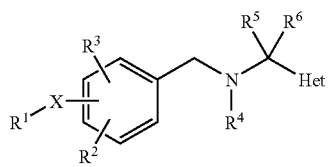

wherein

X is oxygen or sulphur or a $NR^7$ group;

$R^1$ is $C_3$-$C_8$ alkyl, or $C_1$-$C_8$ alkyl substituted by phenoxy or phenyl, both phenoxy or phenyl being optionally substituted by one or more fluoro, chloro, trifluoromethyl, $C_1$-$C_6$ alkyl, hydroxyl, $C_1$-$C_6$ alkoxy;

$R^2$, $R^3$ are independently hydrogen, $C_1$-$C_6$ alkyl, halogen, trifluoromethyl, hydroxy or $C_1$-$C_6$ alkoxy;

$R^4$ is hydrogen, $C_1$-$C_8$ alkyl;

$R^5$, $R^6$ are independently hydrogen, $C_1$-$C_3$ alkyl, optionally substituted by hydroxy or phenyl;

$R^7$ is hydrogen or straight or branched $C_1$-$C_3$ alkyl;

Het is a five to seven membered, saturated or unsaturated heteromonocyclic or an eight to ten membered, saturated or unsaturated heterobicyclic group, containing one or more heteroatoms chosen independently from nitrogen, oxygen and sulphur, said mono- or bicyclic groups being optionally substituted by $C_1$-$C_6$alkyl, halogen, hydroxyl or $C_1$-$C_6$ alkoxy;

and the pharmaceutically acceptable salts or prodrug thereof, that are active as sodium and/or calcium channel modulators and/or as selective MAO-B inhibitors and therefore useful in preventing, alleviating and curing a wide range of pathologies, including, but not limited to, neurological, psychiatric, cardiovascular, inflammatory, ophthalmic, urologic, metabolic and gastrointestinal diseases, where the above mechanisms have been described as playing a pathological role.

BACKGROUND OF THE INVENTION

Chemical Background

WO 02/49993, discloses aryl-substituted heterocyclic derivatives and the use of such compounds in treating a variety of inflammatory and immuno system disorders. U.S. Pat. No. 4,145,439 describes benzyl phenyl ethers and their use for combatting arthropodes, nematodes, fungi and bacteria. WO 03/37865 describes the preparation of pyridinylethyl amines and amides and their use as anticancer drugs. WO 01/14331 describes the preparation of 4-amino-1-benzylpiperidines(piperazines) as antimalarial agents. In U.S. Pat. No. 5,318,988 2-aminomethyl-chromanes are described together with their use in the treatment of CNS diseases. In J. Indian Chem. Soc. 1987, 64, 169-171, the synthesis of benzodioxolano-ethylamines is reported. In Armyanskii Khimicheskii Zhurnal 1968, 21, 509-514, the synthesis of benzodioxan derivatives is described as possible adrenolytic substances. In WO 96/20191, the preparation of 3-(N-aryl and N-heterocyclylaminomethyl)-indole derivatives are described and their use against CNS diseases. In FR patent 2.181.559 indole derivatives are described and their use as anticonvulsant and analgesic agents. In WO 94/26738 benzofuranylurea derivatives and analogues were described as ACAT-inhibitors. In EP 534246 benzylaminoderivatives are described and the use as antiarrhythmic agents. In WO 01/12604, 2-pyridyl derivatives are described as fungicides.

Biological Background

It is well known that sodium channels play an important role in the neuronal network by transmitting electrical impulses rapidly throughout cells and cell networks, thereby coordinating higher processes ranging from locomotion to cognition. These channels are large transmembrane proteins, which are able to switch between different states to enable selective permeability for sodium ions. For this process an action potential is needed to depolarize the membrane, and hence these channels are voltage-gated. In the past few years a much better understanding of sodium channels and drugs interacting with them has been developed.

It has become clear that a number of drugs having an unknown mechanism of action actually act by modulating sodium channel conductance, including local anesthetics, class I antiarrhythmics and anticonvulsants. Neuronal sodium channel blockers have found application with their use in the treatment of epilepsy (phenyloin and carbamazepine), bipolar disorder (lamotrigine), preventing neurodegeneration, and in reducing neuropathic pain. Various anti-epileptic drugs that stabilize neuronal excitability are effective in neuropathic pain (gabapentin).

In addition, an increase in sodium channel expression or activity has also been observed in several models of inflammatory pain, suggesting a role of sodium channels in inflammatory pain.

Calcium channels are membrane-spanning, multi-subunit proteins that allow controlled entry of calcium ions into cells from the extracellular fluid. Commonly, calcium channels are voltage dependent and are referred to as voltage sensitive calcium channels (VSCC). VSCCs are found throughout the mammalian nervous system, where they regulate such varied activities as cellular excitability, transmitter release, intracellular metabolism, neurosecretory activity and gene expression. All "excitable" cells in animals, such as neurons of the central nervous system (CNS), peripheral nerve cells, and muscle cells, including those of skeletal muscles, cardiac muscles and venous and arterial smooth muscles, have voltage dependent calcium channels. Calcium channels have a central role in regulating intracellular calcium ions levels that are important for cell viability and function. Intracellular calcium ion concentrations are implicated in a number of vital processes in animals, such as neurotransmitter release, muscle contraction, pacemaker activity, and secretion of hormones. It is believed that calcium channels are relevant in certain disease states. A number of compounds useful in treating various cardiovascular diseases in mammals, including humans, are thought to exert their beneficial effects by modulating functions of voltage dependant calcium channels present in cardiac and/or vascular smooth muscle. Compounds with activity against calcium channels have also been implicated for the treatment of pain. In particular N-type calcium channels (Cav2.2), responsible for the regulation of neurotransmitters, are thought to play a significant role in nociceptive transmission, both due to their tissue distribution as well as from the results of several pharmacological studies. This hypothesis has been validated in the clinic by Zinocotide, a peptide derived from the venom of the marine snail, Conus Magus. A limitation in the therapeutic use of this peptide is that it has to be administered intrathecally in humans (Bowersox S. S. and Luther R. Toxicon, 1998, 36, 11, 1651-1658).

Monoamine oxidase (MAO) is an integral protein of the outer mitochondrial membrane and plays a major role in the in vivo inactivation of biogenic and diet-derived amines in both the CNS and in peripheral neurons and tissues. Two MAO enzymes are distinguished on the basis of their substrate preferences and sensitivity to inhibition by the MAO inhibitor, clorgyline:

MAO type A (MAO-A) which in the human CNS is responsible for the deamination of serotonin and noradrenaline. The highest MAO-A concentrations are in the catecholaminergic neurons of the locus ceruleus;

MAO-B which is responsible mainly for the catabolism of dopamine. In contrast to the rat brain, MAO-B is the major form in the human and guinea pig CNS. The highest MAO-B concentrations are in the serotoninergic neurons of the raphe nucleus and posterior hypothalamus. The nigral MAO-B is located primarily in glial cells.

MAO-B (but not MAO-A) activity in CNS increases with age in both humans and animals, perhaps as a result of the glial cell proliferation associated with neuronal loss. Increased MAO-B levels in Alzheimer's plaques have also been reported. Increased blood platelet MAO-B activity has been reported in both Alzheimer's (AD) and Parkinson's Disease (PD). MAO-B activity was reduced by 40% in the brain of smokers: tobacco use is associated both with psychiatric disease and with a reduced risk for PD.

Most currently investigated MAO-B inhibitors are irreversible. The inhibition is very persistent (weeks), as its effects can only be overcome by de novo synthesis of the enzyme. Interest in the MAO-B inhibition was initially stimulated by the desire to elevate the reduced striatal DA concentrations characteristic of PD. As increased DA concentration in the synaptic cleft would be expected as the primary effect of treatment with a selective MAO-B inhibitor. In PD, the need to supply the DA precursor L-Dopa, the golden standard PD therapy, should thus be reduced. This is desirable, as L-Dopa, despite the excellent initial improvement achieved, is associated in the longer term with increasingly severe side effects, including motors fluctuations, dyskinesia and dystonia.

In addition to loss of cholinergic neurons, there is a decrease in the levels of the DA, noradrenaline and serotonin in the brains of AD patients. MAO-B activity is significantly increased in the platelets and selected brain regions of AD patients. MAO-B inhibitors may act by both reducing the formation of oxygen radicals and preventing the breakdown of monoamines and thus elevating their level in the brain of AD patients.

Promising results using MAO-B inhibitors were reported also for the treatment of narcolepsy, Tourette's syndrome/attention deficit disorders, negative symptoms of schizophrenia, drug addiction and obesity.

All together these findings indicate that compounds with sodium and/or calcium channel blockade and/or MAO-B inhibition have a high therapeutic potential in preventing, alleviating and curing a wide range of pathologies, including neurological, psychiatric, cardiovascular, urologic, metabolic and gastrointestinal diseases, where the above mechanisms have been described as playing a pathological role.

There are many papers and patents which describe sodium channel and/or calcium channel modulators or antagonists and/or MAO-B inhibitors for the treatment or modulation of a plethora of disorders, such as their use as local anesthetics, antiarrhythmics, antiemetics, antimanic depressants, agents for the treatment of unipolar depression, cardiovascular diseases, urinary incontinence, diarrhea, inflammation, epilepsy, neurodegenerative conditions, nerve cell death, anticonvulsants, neuropathic pain, migraine, acute hyperalgesia and inflammation, renal disease, allergy, asthma, bronchospasm, dysmenorrhea, esophageal spasm, glaucoma, urinary tract disorders, gastrointestinal motility disorders, premature labour, obesity. A largely incomplete list is shown below.

An extensive and thorough prior art overview is reported in WO 03/057219 (and references therein); a further selection of prior art is reported in the following references: Alzheimer, C. Adv. Exp. Med. Biol. 2002, 513, 161-181; Vanegas, H.; Schaible, H. Pain 2000, 85, 9-18; U.S. Pat. No. 5,051,403; U.S. Pat. No. 5,587,454; U.S. Pat. No. 5,863,952; U.S. Pat. No. 6,011,035; U.S. Pat. No. 6,117,841; U.S. Pat. No. 6,362,174; U.S. Pat. No. 6,380,198; U.S. Pat. No. 6,420,383; U.S. Pat. No. 6,458,781; U.S. Pat. No. 6,472,530; U.S. Pat. No. 6,518,288; U.S. Pat. No. 6,521,647; WO 97/10210; WO 03/018561; WO 01/12176; WO 96/37199; U.S. Pat. No. 6,210,706.

DESCRIPTION OF THE INVENTION

This invention is related to benzylaminomethylene heterocycles of the following general formula (I)

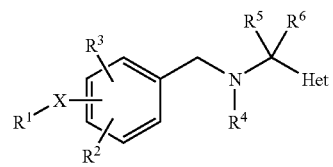

wherein

X is oxygen or sulphur or a $NR^7$ group;

$R^1$ is $C_3$-$C_8$ alkyl, or $C_1$-$C_6$ alkyl substituted by phenoxy or phenyl, both phenoxy or phenyl being optionally substituted by one or more fluoro, chloro, trifluoromethyl, $C_1$-$C_6$ alkyl, hydroxyl, $C_1$-$C_6$ alkoxy;

$R^2$, $R^3$ are independently hydrogen, $C_1$-$C_6$ alkyl, halogen, trifluoromethyl, hydroxy or $C_1$-$C_6$ alkoxy;

$R^4$ is hydrogen, $C_1$-$C_8$ alkyl;

$R^5$, $R^6$ are independently hydrogen, $C_1$-$C_3$ alkyl, optionally substituted by hydroxy or phenyl;

$R^7$ is hydrogen or straight or branched $C_1$-$C_3$ alkyl;

Het is a five to seven membered, saturated or unsaturated heteromonocyclic or an eight to ten membered, saturated or unsaturated heterobicyclic group, containing one or more heteroatoms chosen independently from nitrogen, oxygen and sulphur, said mono- or bicyclic groups being optionally substituted by $C_1$-$C_6$alkyl, halogen, hydroxyl or $C_1$-$C_6$ alkoxy;

and the pharmaceutically acceptable salts thereof, with the proviso that:

Het cannot be indole (FR 2,181,559), benzo[b]furan (WO 94/26738), benzo[b]thiophen (WO 94/26738), chroman (U.S. Pat. No. 5,318,988), when $R^5$ and $R^6$ are both hydrogen, or 2-pyridyl (WO 01/12604);

when $R^1$ is unsubstituted or substituted benzyl, and $R^2$ and $R^3$ are hydrogen, halogen or alkoxy, $R^4$ is other than hydrogen (U.S. Pat. No. 4,145,439);

when $R^1$ is propyl or butyl, $R^2$, $R^3$, $R^5$ and $R^6$ are hydrogen and $R^4$ is hydrogen, methyl or ethyl, Het cannot be 1,4-benzodioxan (Mndzhoyan et al. Armyanskii Khimicheskii Zhurnal 1968, 21, 509-514);

when X—R¹ is a para butyloxy group and R², R³, R⁴, R⁵ and R⁶ are hydrogen, Het cannot be 2-thiophenyl, (U.S. Pat. No. 4,623,662) or 4-(2,2'-dimethyl)-pyranyl (Arutyunian, N. S. et al. Armyanskii Khimicheskii Zhurnal 1984, 37, 749-753);

when X—R¹ is an ortho heptyloxy or octyloxy group and R², R³, R⁴, R⁵ and R⁶ are hydrogen, Het cannot be 2-furyl (commercial library);

when X—R¹ is an ortho O—$(CH_2)_m$-p-$CF_3$-phenyl group, where m is an integer from 1 to 3, and R², R³, R⁵ and R⁶ are hydrogen, Het cannot be pyridyl (EP 534246).

The optional substituents in the phenyl ring may be in any position. The pharmaceutically acceptable salts of the compounds of formula I include acid addition salts with inorganic acids, e.g. hydrochloric, hydrobromic, sulphuric, and phosphoric or organic acids, e.g. acetic, propionic, benzoic, cinnamic, mandelic, salicylic, glycolic, lactic, oxalic, malic, maleic, malonic, fumaric, tartaric, citric, and the like.

The invention also relates to the use of the compounds of formula I

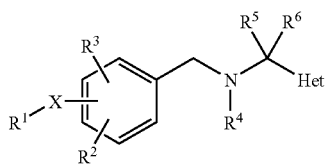

I wherein
X is oxygen or sulphur or a $NR^7$ group;
R¹ is $C_3$-$C_8$ alkyl, or $C_1$-$C_8$ alkyl substituted by phenoxy or phenyl, both phenoxy or phenyl being optionally substituted by one or more fluoro, chloro, trifluoromethyl, $C_1$-$C_6$ alkyl, hydroxyl, $C_1$-$C_6$ alkoxy;
R², R³ are independently hydrogen, $C_1$-$C_6$ alkyl, halogen, trifluoromethyl, hydroxy or $C_1$-$C_6$ alkoxy;
R⁴ is hydrogen, $C_1$-$C_8$ alkyl;
R⁵, R⁶ are independently hydrogen, $C_1$-$C_3$ alkyl, optionally substituted by hydroxy or phenyl;
R⁷ is hydrogen or straight or branched $C_1$-$C_3$ alkyl;
Het is a five to seven membered, saturated or unsaturated heteromonocyclic or an eight to ten membered, saturated or unsaturated heterobicyclic group, containing one or more heteroatoms chosen independently from nitrogen, oxygen and sulphur, said mono- or bicyclic groups being optionally substituted by $C_1$-$C_6$alkyl, halogen, hydroxyl or $C_1$-$C_6$ alkoxy;
and the pharmaceutically acceptable salts thereof, with the proviso that:
Het cannot be an indole (FR 2,181,559), chroman (U.S. Pat. No. 5,318,988), when R⁵ and R⁶ are both hydrogen;
when X—R¹ is an ortho O—$(CH_2)_m$-p-$CF_3$-phenyl group, where m is an integer from 1 to 3, and R², R³, R⁵ and R⁶ are hydrogen, Het cannot be pyridyl (EP 534246).

For the preparation of a medicament having sodium and/or calcium channel modulating activity and/or selective MAO-B inhibiting activity.

Preferred use compounds of the invention are the compounds of formula I wherein R¹ is benzyl or $C_5$-$C_8$ alkyl, R⁴, R⁵, and R⁶ are hydrogen or $C_1$-$C_3$ alkyl, X is oxygen and Het is furan, tetrahydrofuran, isoxazol, oxazol, thiophen, pyran, dioxane, unsubstituted or substituted by $C_1$-$C_3$ alkyl.

Examples of specific compounds of the invention are:
(4-Pentyloxy-benzyl)-(furan-2-ylmethyl)-amine;
(4-Heptyloxy-benzyl)-(furan-2-ylmethyl)-amine;
(R)(4-Pentyloxy-benzyl)-(tetrahydro-furan-2-ylmethyl)-amine;
(S)(4-Pentyloxy-benzyl)-(tetrahydro-furan-2-ylmethyl)-amine;
(R)(4-Heptyloxy-benzyl)-(tetrahydro-furan-2-ylmethyl)-amine;
(S)(4-Heptyloxy-benzyl)-(tetrahydro-furan-2-ylmethyl)-amine;
(R)(4-Pentyloxy-benzyl)-(tetrahydro-pyran-2-ylmethyl)-amine;
(S)(4-Pentyloxy-benzyl)-(tetrahydro-pyran-2-ylmethyl)-amine;
(R)(4-Heptyloxy-benzyl)-(tetrahydro-pyran-2-ylmethyl)-amine;
(S)(4-Heptyloxy-benzyl)-(tetrahydro-pyran-2-ylmethyl)-amine;
(4-Benzyloxy-benzyl)-(furan-2-ylmethyl)-amine;
(4-Benzyloxy-benzyl)-(5-methyl-furan-2-ylmethyl)-amine;
[4-(3-Fluoro-benzyloxy)-benzyl]-(furan-2-ylmethyl)-amine;
[4-(3-Chloro-benzyloxy)-benzyl]-(furan-2-ylmethyl)-amine;
[4-(3-Fluoro-benzyloxy)-benzyl]-(5-methyl-furan-2-ylmethyl)-amine;
[4-(3-Chloro-benzyloxy)-benzyl]-(5-methyl-furan-2-ylmethyl)-amine;
(R)(4-Benzyloxy-benzyl)-[1-(furan-2-yl)-1-ethyl]-amine;
(S)(4-Benzyloxy-benzyl)-[1-(furan-2-yl)-1-ethyl]-amine;
[4-(3-Fluoro-benzyloxy)-benzyl]-[1-(furan-2-yl)-1-ethyl]-amine;
[4-(3-Chloro-benzyloxy)-benzyl]-[1-(furan-2-yl)-1-ethyl]-amine;
(R)(4-Benzyloxy-benzyl)-(tetrahydro-furan-2-ylmethyl)-amine;
(S)(4-Benzyloxy-benzyl)-(tetrahydro-furan-2-ylmethyl)-amine;
(R)[4-(3-Fluoro-benzyloxy)-benzyl]-(tetrahydro-furan-2-ylmethyl)-amine;
(S)[4-(3-Fluoro-benzyloxy)-benzyl]-(tetrahydro-furan-2-ylmethyl)-amine;
(R)[4-(3-Chloro-benzyloxy)-benzyl]-(tetrahydro-furan-2-ylmethyl)-amine;
(S)[4-(3-Chloro-benzyloxy)-benzyl]-(tetrahydro-furan-2-ylmethyl)-amine;
(R)[4-(3-Fluoro-benzyloxy)-benzyl]-(tetrahydro-pyran-2-ylmethyl)-amine;
(S)[4-(3-Fluoro-benzyloxy)-benzyl]-(tetrahydro-pyran-2-ylmethyl)-amine;
(R)[4-(3-Chloro-benzyloxy)-benzyl]-(tetrahydro-pyran-2-ylmethyl)-amine;
(S)[4-(3-Chloro-benzyloxy)-benzyl]-(tetrahydro-pyran-2-ylmethyl)-amine;
(4-Benzyloxy-benzyl)-(1,4-dioxan-2-ylmethyl)-amine;
[4-(3-Chloro-benzyloxy)-benzyl]-(pyrido-2-ylmethyl)-amine;
[4-(3-Chloro-benzyloxy)-benzyl]-(pyrido-3-ylmethyl)-amine;
[4-(3-Chloro-benzyloxy)-benzyl]-(pyrido-4-ylmethyl)-amine;
[4-(3-Chloro-benzyloxy)-benzyl]-(imidazol-2-ylmethyl)-amine;
[4-(3-Chloro-benzyloxy)-benzyl]-(1-methyl-imidazol-2-ylmethyl)-amine;
[4-(3-Chloro-benzyloxy)-benzyl]-(5-methyl-1H-triazol-2-ylmethyl)-amine;

[4-(3-Chloro-benzyloxy)-benzyl]-(4-methyl-thiazol-2-ylmethyl)-amine;
(4-Benzyloxy-benzyl)-(isoxazol-5-ylmethyl)-amine;
[4-(3-Fluoro-benzyloxy)-benzyl]-(isoxazol-5-ylmethyl)-amine;
[4-(3-Chloro-benzyloxy)-benzyl]-(is oxazol-5-ylmethyl)-amine;
(4-Benzyloxy-benzyl)-(3-methyl-isoxazol-5-ylmethyl)-amine;
[4-(3-Fluoro-benzyloxy)-benzyl]-(3-methyl-isoxazol-5-ylmethyl)-amine;
[4-(3-Chloro-benzyloxy)-benzyl]-(3-methyl-isoxazol-5-ylmethyl)-amine;
(4-Benzyloxy-benzyl)-(oxazol-2-ylmethyl)-amine;
[4-(3-Fluoro-benzyloxy)-benzyl]-(oxazol-2-ylmethyl)-amine;
[4-(3-Chloro-benzyloxy)-benzyl]-(oxazol-2-ylmethyl)-amine;
(4-Benzyloxy-benzyl)-(oxazol-5-ylmethyl)-amine;
[4-(3-Fluoro-benzyloxy)-benzyl]-(oxazol-5-ylmethyl)-amine;
[4-(3-Chloro-benzyloxy)-benzyl]-(oxazol-5-ylmethyl)-amine;
(4-Benzyloxy-benzyl)-(thiophen-2-ylmethyl)-amine;
[2-(3-Chloro-benzyloxy)-benzyl]-(thiophen-2-ylmethyl)-amine;
[2-(3-Fluoro-benzyloxy)-benzyl]-(thiophen-2-ylmethyl)-amine;
[3-(3-Chloro-benzyloxy)-benzyl]-(thiophen-2-ylmethyl)-amine;
[3-(3-Fluoro-benzyloxy)-benzyl]-(thiophen-2-ylmethyl)-amine;
[4-(3-Chloro-benzyloxy)-benzyl]-(thiophen-2-ylmethyl)-amine;
[4-(3-Fluoro-benzyloxy)-benzyl]-(thiophen-2-ylmethyl)-amine;
[2-(3-Fluoro-benzyloxy)-benzyl]-(benzo[b]furan-2-ylmethyl)-amine;
[3-(3-Fluoro-benzyloxy)-benzyl]-(benzo[b]furan-2-ylmethyl)-amine;
[4-(3-Fluoro-benzyloxy)-benzyl]-(benzo[b]furan-2-ylmethyl)-amine;
(R)[4-(3-Fluoro-benzyloxy)-benzyl]-(dihydro-benzo[b]furan-2-ylmethyl)-amine;
(S)[4-(3-Fluoro-benzyloxy)-benzyl]-(dihydro-benzo[b]furan-2-ylmethyl)-amine;
[4-(3-Chloro-benzyloxy)-benzyl]-(benzimidazol-2-ylmethyl)-amine;
either as a single isomer or as a mixture of isomers thereof, and the pharmaceutically acceptable salts thereof.

The compounds of the invention and the salts thereof can be obtained by a process comprising:
a) reaction of compounds of formula II

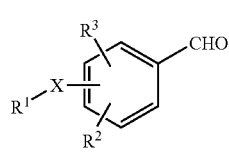

wherein $R^1$, $R^2$, $R^3$ and X are as defined above with compounds of formula III, in the presence of a reducing agent

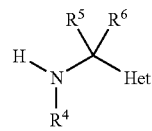

wherein $R^4$, $R^5$, $R^6$ and Het are as defined previously thus obtaining a compound of formula I; or
b) reaction of compounds of formula IV

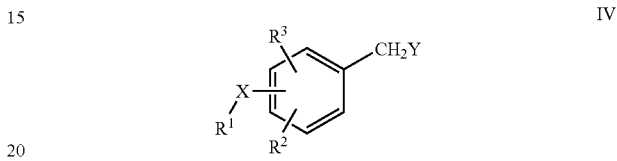

wherein $R^1$, $R^2$, $R^3$ and X are as defined above and Y is a halogen atom or a O-EWG group, where the EWG means an electron withdrawing group, like e.g. mesyl, tosyl or trifluoroacetyl groups, able to transform the oxygen which they are linked to, in a good leaving group with compounds of formula III and, if desired, converting a compound of the invention into another compound of the invention and/or, if desired, converting a compound of the invention into a pharmaceutically acceptable salt and/or, if desired, converting a salt into a free compound.

Compounds II-IV are commercially available compounds or are prepared from commercially available compounds using well-known methods.

The reaction compounds of formula II with compounds of formula III to give the compounds of formula I is a reductive amination reaction which can be carried out according to well known methods. According to a preferred embodiment of the invention, it may be performed under nitrogen atmosphere, in a suitable organic solvent, such as an alcohol, e.g. a lower alkanol, in particular methanol, or in acetonitrile, or in tetrahydrofuran, at a temperature ranging from about 0° C. to about 70° C., in the presence of a reducing agent, the most appropriate being sodium borohydride or sodium cyanoborohydride. Occasionally titanium IV isopropylate and molecular sieves can be added to the reaction mixture for facilitating the reaction.

In a compound of formula IV the halogen is preferably bromine or iodine. The alkylation reaction of a compound of formula IV with a compound of formula III can be carried out in a suitable organic solvent, such as an alcohol, e.g. methanol, ethanol or isopropanol, in particular in ethanol, at a temperature ranging from about 0° C. to about 50° C.

The optional salification of a compound of the invention as well as the conversion of a salt into the free compound may be carried out by conventional methods.

When in the compounds of the present invention and in the intermediate-products thereof, groups are present, which need to be protected before submitting them to the above illustrated reactions, they may be protected before being reacted and then deprotected according to well-known methods.

Pharmacology

The compounds of the invention display affinities for the calcium and/or sodium channel binding sites as demonstrated using selective radioligands in in vitro binding studies.

The compounds according to the invention are blockers of the voltage dependent sodium channels and/or calcium channels. These compounds therefore displace 3H-batrachotoxin (BTX) with a high affinity from the binding site on the sodium channel, with $IC_{50}$ in the low µM or sub µM range. Similarly the compounds displace 3H-nitrendipine from the binding site in the calcium channel, with $IC_{50}$ in the low µM or most usually in the sub µM range as well as inhibiting calcium influx induced through calcium channels via cellular depolarisation.

The voltage dependent block of the calcium and/or sodium channels by the compounds of the invention has also been demonstrated by fluorescence calcium influx assay and electrophysiological studies.

The N-type calcium channel modulating activity of the heterocyclic compounds of general formula I was measured through a fluorescence based calcium influx assay.

The sodium channel modulating activity of the compounds of general formula I was measured through electrophysiological assays using the two electrodes voltage clamp (TEVC) technique in isolated *Xenopus* oocytes expressing the Na channel Nav 1.3.

Such substances exhibit "use-dependency" when the sodium channels are blocked i.e. maximum blockage of the sodium channels is only achieved after repeated stimulation of the sodium channel. Consequently, the substances preferably bind to sodium channels which are multiply activated. As a result the substances are capable of activity preferentially in those regions of the body which are pathologically overstimulated, as illustrated by patch-clamp experiments (W. A. Catteral, Trends Pharmacol. Sci., 8, 57-65; 1987) which show that the compounds according to the invention block the electrically stimulated sodium channel in a "use-dependent" manner.

As a consequence of these mechanisms the compounds of the invention are active in vivo when orally administered in the range of 0.1 to 100 mg/kg in a wide range of animal models and in particular in the MES test of electrically-induced convulsions, in the formalin model of persistent pain and in the carragenan model of inflammation.

The compounds of this invention beyond being potent calcium and/or sodium channels blockers are also able to selectively and reversibly inhibit MAO-B both in vitro and in vivo.

The compounds of the invention that are potent inhibitors of MAO-B ($IC_{50}$ in the submicromolar range) have generally no relevant effect on MAO-A. In enzymatic studies using rat brain membranes and selective radiolabelled substrates, the compounds are generally over 1000 times more active as MAO-B inhibitors than MAO-A inhibitors. The MAO-B inhibition by the compounds is not time-dependent and the enzyme activity fully recovers after washings as it is typical for reversible inhibitors.

After oral administration in mice, the compounds behave as potent and reversible, short-acting MAO-B inhibitors with full recovery of activity 24 h after treatment.

In view of the above described mechanisms of action, the compounds of the present invention are useful in the treatment or prevention of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions.

Compounds of the invention are also useful for the treatment of chronic pain. Chronic pain includes, and is not limited to, chronic pain caused by inflammation or an inflammatory-related condition, ostheoarthritis, rheumatoid arthritis or as sequela to disease, acute injury or trauma and includes upper back pain or lower back pain (resulting from systematic, regional or primary spine disease (such as radiculopathy), bone pain (due to osteoarthritis, osteoporosis, bone metastasis or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, temporomandibular joint syndrome, gout, fibrosis or thoracic outlet syndromes.

Compounds of the invention are also useful in the treatment of acute pain (caused by acute injury, illness, sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea, endometriosis or surgery (such as open heart or bypass surgery), post operative pain, kidney stone pain, gallbladder pain, gallstone pain, obstetric pain or dental pain.

Compounds of the invention are also useful in the treatment of migraine, such as tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds of the invention are also useful for the treatment of neurological conditions and cognitive disorders. Neurological conditions include, and are not limited to, conditions such as epilepsy (including simple partial seizures, complex partial seizures, secondary generalised seizures, further including absence seizures, myoclonic seizures, clonic seizures, tonic seizures, tonic clonic seizures and atonic seizures), degenerative dementia (including senile dementia, Alzheimer's disease, Pick's disease, Huntington's chorea, Parkinson's disease and Creutzfeldt-Jakob disease), and vascular dementia (including multi-infarct dementia, stroke and cerebral ischemia), as well as dementia associated with intracranial space occupying lesions, trauma, infections and related conditions (including HIV infection), metabolism, toxins, anoxia and vitamin deficiency; and mild cognitive impairment associated with aging, particularly age associated memory impairment, movement disorders (postencephalitic parkinsonism, progressive supranuclear palsy, corticobasal degeneration, restless leg syndrome), narcolepsy, deficit and hyperactivity disorders (ADHD), Tourette's Syndrome, amyotrophic lateral sclerosis, Down's syndrome.

Compounds of the invention are also useful for the treatment of psychiatric disorders. Psychiatric disorders include, and are not limited to, manic depression also known as bipolar disorder (such as bipolar disorder type I, bipolar disorder type II), cyclothymic disorder, rapid cycling, ultradian cycling, bipolar depression, acute mania, mania, mixed mania, hypomania or unipolar depression, schizophrenia, schizophreniform disorders, schizoaffective disorders, delusional disorders, brief psychotic disorders, shared psychotic disorders, psychotic disorder due to a general medical condition, substance-induced psychotic disorders or a psychotic disorder not otherwise specified, anxiety disorders and moreover in smoke and drug addiction.

Compounds of the invention are also useful in the treatment of peripheral diseases such as tinnitus, muscle spasm, muscular sclerosis, and other disorders, including, and not limited to cardiovascular diseases (such as cardiac arrhythmia, cardiac infarction or angina pectoris, hypertension, hypoxia, cardiac ischemia) endocrine disorders (such as acromegaly or diabetes insipidus), diseases in which the pathophysiology of the disorder involves excessive or hypersecretory or otherwise inappropriate cellular secretion of an endogeneous substance (such as catecholamine, a hormone or a growth factor).

Compounds of the invention are also useful in the treatment of liver disease, such as inflammatory liver disease, for example chronic viral hepatitis B, chronic viral hepatitis C, alcoholic liver injury, primary biliary cirrhosis, autoimmune hepatitis, non-alcoholic steatohepatitis and liver transplant rejection.

Compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gut, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarteritis nodosa, thyroiditis, aplastic anaemia, scleroderma, myasthenia gravis, multiple sclerosis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyresis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexitics, pelvic inflammation, bartolinities and vaginitis.

Compounds of the invention are also useful in the treatment of ophthalmic diseases such as retinitis, retinopathies, uveitis and acute injury to the eye tissue, macular degeneration or glaucoma, conjunctivitis.

Compounds of the invention are also useful in the treatment of obesity.

Compounds of the invention are also useful for the treatment of all other conditions mediated by the inhibition of voltage gated sodium channels and/or voltage gated calcium channels and/or MAO-B.

It will be appreciated that the compounds of the invention may advantageously be used in conjunction with one or more other therapeutic agents. Examples of suitable agents for adjunctive therapy include L-Dopa or a dopamine agonists, a $5HT_{1B/1D}$ agonist, such as a triptan (e.g. sumatriptan or naratriptan); an adenosine A1 agonist; an EP ligand; an NMDA modulator, such as a glycine antagonist; a substance P antagonist (e.g. an NK1 antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptiline); a neurone stabilising antiepileptic drug; a monoaminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumor necrosis factor alpha; an antibody therapy, such as monoclonal antibody therapy; an antiviral agent, such as a nucleoside inhibitor (e.g. lamivudine) or an immune system modulator (e.g. interferon); an analgesic, such as a cyclooxygenase-2 inhibitor; a local anaesthetic; a stimulant, including caffeine; an H2-antagonist (e.g. ranitidine); a proton pump inhibitor (e.g. omeprazole); an antacid (e.g. aluminium or magnesium hydroxide; an antiflatulent (e.g. semethicone); a decongestant (e.g. phenylephrine, phenylpropanolamine, pseudoephedrine, oxymetazoline, epinephrine, naphazoline, xylometazoline, propylhexedrine, or levo-desoxyephedrine, naphazoline, xylometazoline, propylhexedrine, or levo-desoxyephedrine); antitussive (e.g. codeine, hydrocodone, carmiphen, carbetapentane, or dextramethorphan); a diuretic; or a sedating or non-sedating antihistamine. It is to be understood that the present invention covers the use of a compound of formula (I) or a pharmaceutically acceptable salt thereof in combination with one or more therapeutic agents.

The compounds of the present invention are useful in human and veterinary medicine. It is to be understood that reference to treatment includes both treatments of established symptoms and prophylactic treatment, unless explicitly stated otherwise.

The benzylaminoalkylene heterocycles derivatives of formula I as above defined can be administered as the "active ingredient" of a pharmaceutically acceptable composition which can be prepared by conventional procedures, for instance by mixing the active ingredient with pharmaceutically acceptable, therapeutically inert organic and/or inorganic carrier materials.

The composition comprising the above defined benzylaminoalkylene heterocycles derivatives can be administered in a variety forms, e.g. orally, in the form of tablets, troches, capsules, sugar or film coated tablets, liquid solutions, emulsions or suspensions; rectally, in the form of suppositories; parenterally, e.g. by intramuscular or intravenous injection or infusion; and transdermally.

Suitable pharmaceutically acceptable, therapeutically inert organic and/or inorganic carrier materials useful in the preparation of such composition include, for example, water, gelatin, gum arabic, lactose, starch, cellulose, magnesium stearate, talc, vegetable oils, polyalkyleneglycols and the like. The composition comprising the benzylaminoalkylene heterocycles derivatives of formula I as above defined can be sterilized and may contain further well known components, such as, for example, preservatives, stabilizers, wetting or emulsifying agents, e.g. paraffin oil, mannide monooleate, salts to adjust osmotic pressure, buffers and the like.

For example, the solid oral forms may contain, together with the active ingredient, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disgregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The oral formulations comprise sustained release formulations that can be prepared in conventional manner, for instance by applying an enteric coating to tablets and granules.

The liquid dispersion for oral administration may be e.g. syrups, emulsions and suspensions.

The syrups may contain as carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain, together with the active ingredient, a pharmaceutically acceptable carrier, e.g. cocoa butter, polyethylene glycol, a polyoxyethylene sorbitan fatty acid ester surfactants or lecithin.

The composition comprising the benzylaminoalkylene heterocycles derivatives of formula I as above defined is generally in the form of a dose unit containing, for example, 0.1 mg to 100 mg of active ingredient per unit dosage form.

Suitable treatment is given 1, 2 or 3 times daily, depending upon clearance rate. Accordingly, the desired dose may be presented in a single dose or as divided doses administered at appropriate intervals, for example two to four or more sub-doses per day.

The pharmaceutical compositions comprising the benzylaminoalkylene heterocycles derivatives of formula I as above defined will contain, per dosage unit, e.g., capsule, tablet, powder injection, teaspoonful, suppository and the like from about 0.1 to about 500 mg of the active ingredient most preferably from 1 to 10 mg.

Optimal therapeutically effective doses to be administered may be readily determined by those skilled in the art and will vary, basically, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

The invention is further illustrated by the following examples.

EXAMPLE 1

[4-(3-Chloro-benzyloxy)-benzyl]-(3-methyl-isoxazol-5-ylmethyl)-amine

A 1 M solution of (3-methyl-isoxazol-5-yl)-methylamine (100.9 mg, 0.9 mmol) in dry methanol was added to a 0.1 M solution of 4-(3-chloro-benzyloxy)-benzaldehyde (197.4 mg, 0.8 mmol), prepared as described in Example 3, in dry methanol. 4 Å molecular sieves (150 mg) were added and the reaction mixture was stirred 12 hours at room temperature under nitrogen.

A 0.5 M solution of sodium borohydride (36.6 mg, 0.97 mmol) in dry methanol was added and the resulting mixture was stirred overnight at room temperature.

A 20% solution of citric acid was added (pH 5) and the crude mixture was passed through a SCX cartridge (Strong Cation Exchange resin). A mixture of the desired product and (3-methyl-isoxazol-5-yl)-methylamine were recovered by elution with 3% ammonia solution in methanol.

After solvent evaporation, the residue was dissolved in dichloromethane (10 ml) and treated with beads of PS-benzaldehyde (227 mg, 0.25 mmol). After resin filtration, the solvent was evaporated to dryness and 215 mg of the title compound was obtained, yield 80%.

MS (ESI Pos Spray 4 kV; Skimmer 20 V; Probe 300° C.): 343.01 (MH+); 231.1 [M-NHR]H+

$^1$H-NMR (CDCl$_3$+D$_2$O+Na$_2$CO$_3$) δ: 7.43 (s br, 1H); 7.30 (m, 2H); 7.24 (d, 2H); 6.92 (d, 2H); 5.98 (s, 1H); 5.03 (s, 2H); 3.85 (s, 2H); 3.74 (s, 2H); 2.29 (s, 3H).

EXAMPLE 2

(R)[4-(3-Chloro-benzyloxy)-benzyl]-(tetrahydro-furan-2-ylmethyl)-amine

A 1 M solution of (tetrahydro-furan-2-yl)-methylamine (91.0 mg, 0.9 mmol) in dry methanol was added to a 0.1 M solution of 4-(3-chloro-benzyloxy)-benzaldehyde (197.4 mg, 0.8 mmol), prepared as described in Example 3, in dry methanol. 4 Å molecular sieves (150 mg) were added and the reaction mixture was stirred 12 hours at room temperature under nitrogen.

A 0.5 M solution of sodium borohydride (36.6 mg, 0.97 mmol) in dry methanol was added and the resulting mixture was stirred overnight at room temperature.

A 20% solution of citric acid was added (pH 5) and the crude mixture was passed through a SCX cartridge (Strong Cation Exchange resin). A mixture of the desired product and (tetrahydro-furan-2-yl)-methylamine was recovered by elution with 3% ammonia solution in methanol.

After solvent evaporation, the residue was dissolved in dichloromethane (10 ml) and treated with beads of PS-benzaldehyde (227 mg, 0.25 mmol). After resin filtration, the solvent was evaporated to dryness and 180 mg of the title compound was obtained, yield 70%.

MS (ESI Pos Spray 4 kV; Skimmer 20 V; Probe 300° C.): 332.0 (MH+); 231.1 [M-NHR]H+

$^1$H-NMR (CDCl$_3$+D$_2$O+Na$_2$CO$_3$) δ: 7.43 (s br, 1H); 7.33-7.21 (m, 5H); 6.92 (d, 2H); 5.03 (s, 2H); 4.08-3.96 (m, 1H); 3.86-3.68 (m, 4H); 2.77-2.61 (m, 2H); 2.02-1.80 (m, 3H); 1.62-1.49 (m, 1H).

Similarly the following compounds were prepared:
(4-Pentyloxy-benzyl)-(furan-2-ylmethyl)-amine;
(4-Heptyloxy-benzyl)-(furan-2-ylmethyl)-amine;
(R)(4-Pentyloxy-benzyl)-(tetrahydro-furan-2-ylmethyl)-amine;
(S)(4-Pentyloxy-benzyl)-(tetrahydro-furan-2-ylmethyl)-amine;
(R)(4-Heptyloxy-benzyl)-(tetrahydro-furan-2-ylmethyl)-amine;
(S)(4-Heptyloxy-benzyl)-(tetrahydro-furan-2-ylmethyl)-amine;
(R)(4-Pentyloxy-benzyl)-(tetrahydro-pyran-2-ylmethyl)-amine;

(S)(4-Pentyloxy-benzyl)-(tetrahydro-pyran-2-ylmethyl)-amine;
(R)(4-Heptyloxy-benzyl)-(tetrahydro-pyran-2-ylmethyl)-amine;
(S)(4-Heptyloxy-benzyl)-(tetrahydro-pyran-2-ylmethyl)-amine;
(4-Benzyloxy-benzyl)-(furan-2-ylmethyl)-amine;
(4-Benzyloxy-benzyl)-(5-methyl-furan-2-ylmethyl)-amine;
[4-(3-Fluoro-benzyloxy)-benzyl]-(furan-2-ylmethyl)-amine;
[4-(3-Chloro-benzyloxy)-benzyl]-(furan-2-ylmethyl)-amine;
[4-(3-Fluoro-benzyloxy)-benzyl]-(5-methyl-furan-2-ylmethyl)-amine;
[4-(3-Chloro-benzyloxy)-benzyl]-(5-methyl-furan-2-ylmethyl)-amine;
(R)(4-Benzyloxy-benzyl)-[1-(furan-2-yl)-1-ethyl]-amine;
(S)(4-Benzyloxy-benzyl)-[1-(furan-2-yl)-1-ethyl]-amine;
[4-(3-Fluoro-benzyloxy)-benzyl]-[1-(furan-2-yl)-1-ethyl]-amine;
[4-(3-Chloro-benzyloxy)-benzyl]-[1-(furan-2-yl)-1-ethyl]-amine;
(R)(4-Benzyloxy-benzyl)-(tetrahydro-furan-2-ylmethyl)-amine;
(S)(4-Benzyloxy-benzyl)-(tetrahydro-furan-2-ylmethyl)-amine;
(R)[4-(3-Fluoro-benzyloxy)-benzyl]-(tetrahydro-furan-2-ylmethyl)-amine;
(S)[4-(3-Fluoro-benzyloxy)-benzyl]-(tetrahydro-furan-2-ylmethyl)-amine;
(S)[4-(3-Chloro-benzyloxy)-benzyl]-(tetrahydro-furan-2-ylmethyl)-amine;
(R)[4-(3-Fluoro-benzyloxy)-benzyl]-(tetrahydro-pyran-2-ylmethyl)-amine;
(S)[4-(3-Fluoro-benzyloxy)-benzyl]-(tetrahydro-pyran-2-ylmethyl)-amine;
(R)[4-(3-Chloro-benzyloxy)-benzyl]-(tetrahydro-pyran-2-ylmethyl)-amine;
(S)[4-(3-Chloro-benzyloxy)-benzyl]-(tetrahydro-pyran-2-ylmethyl)-amine;
(4-Benzyloxy-benzyl)-(1,4-dioxan-2-ylmethyl)-amine;
[4-(3-Chloro-benzyloxy)-benzyl]-(pyrido-2-ylmethyl)-amine;
[4-(3-Chloro-benzyloxy)-benzyl]-(pyrido-3-ylmethyl)-amine;
[4-(3-Chloro-benzyloxy)-benzyl]-(pyrido-4-ylmethyl)-amine;
[4-(3-Chloro-benzyloxy)-benzyl]-(imidazol-2-ylmethyl)-amine;
[4-(3-Chloro-benzyloxy)-benzyl]-(1-methyl-imidazol-2-ylmethyl)-amine;
[4-(3-Chloro-benzyloxy)-benzyl]-(5-methyl-1H-triazol-2-ylmethyl)-amine;
[4-(3-Chloro-benzyloxy)-benzyl]-(4-methyl-thiazol-2-ylmethyl)-amine;
(4-Benzyloxy-benzyl)-(isoxazol-5-ylmethyl)-amine;
[4-(3-Fluoro-benzyloxy)-benzyl]-(isoxazol-5-ylmethyl)-amine;
[4-(3-Chloro-benzyloxy)-benzyl]-(isoxazol-5-ylmethyl)-amine;
(4-Benzyloxy-benzyl)-(3-methyl-isoxazol-5-ylmethyl)-amine;
[4-(3-Fluoro-benzyloxy)-benzyl]-(3-methyl-isoxazol-5-ylmethyl)-amine;
(4-Benzyloxy-benzyl)-(oxazol-2-ylmethyl)-amine;
[4-(3-Fluoro-benzyloxy)-benzyl]-(oxazol-2-ylmethyl)-amine;
[4-(3-Chloro-benzyloxy)-benzyl]-(oxazol-2-ylmethyl)-amine;
(4-Benzyloxy-benzyl)-(oxazol-5-ylmethyl)-amine;
[4-(3-Fluoro-benzyloxy)-benzyl]-(oxazol-5-ylmethyl)-amine;
[4-(3-Chloro-benzyloxy)-benzyl]-(oxazol-5-ylmethyl)-amine;
(4-Benzyloxy-benzyl)-(thiophen-2-ylmethyl)-amine;
[2-(3-Chloro-benzyloxy)-benzyl]-(thiophen-2-ylmethyl)-amine;
[2-(3-Fluoro-benzyloxy)-benzyl]-(thiophen-2-ylmethyl)-amine;
[3-(3-Chloro-benzyloxy)-benzyl]-(thiophen-2-ylmethyl)-amine;
[3-(3-Fluoro-benzyloxy)-benzyl]-(thiophen-2-ylmethyl)-amine;
[4-(3-Chloro-benzyloxy)-benzyl]-(thiophen-2-ylmethyl)-amine;
[4-(3-Fluoro-benzyloxy)-benzyl]-(thiophen-2-ylmethyl)-amine;
[2-(3-Fluoro-benzyloxy)-benzyl]-(benzo[b]furan-2-ylmethyl)-amine;
[3-(3-Fluoro-benzyloxy)-benzyl]-(benzo[b]furan-2-ylmethyl)-amine;
[4-(3-Fluoro-benzyloxy)-benzyl]-(benzo[b]furan-2-ylmethyl)-amine;
(R)[4-(3-Fluoro-benzyloxy)-benzyl]-(dihydro-benzo[b]furan-2-ylmethyl)-amine;
(S)[4-(3-Fluoro-benzyloxy)-benzyl]-(dihydro-benzo[b]furan-2-ylmethyl)-amine;
[4-(3-Chloro-benzyloxy)-benzyl]-(benzimidazol-2-ylmethyl)-amine;

EXAMPLE 3

4-(3-Chloro-benzyloxy)-benzaldehyde

A 0.5 M solution of 1-bromomethyl-3-chloro-benzene (102.7 mg, 0.5 mmol) in acetone was added to a suspension of 4-hydroxy-benzaldehyde (67.2 mg, 0.55 mmol), $K_2CO_3$ (207.3 mg, 1.5 mmol) and KI (10.8 mg, 0.065 mmol) in acetone (7 ml). The reaction mixture was stirred for 2 hours at 70° C.

After cooling, the solid residue was filtered off and the solvent was evaporated under vacuum. The residue was dissolved in ethyl acetate and the organic layer washed twice with 1 M NaOH and dried over $Na_2SO_4$. The title compound was obtained (85 mg) after evaporating the solvent under vacuum, yielding 96.6%.

EXAMPLE 4

In Vitro MAO-A and MAO-B Enzyme Activities Assay

Membrane preparations (crude mitochondrial fraction): male Wistar rats (Harlan, Italy—175-200 g) were sacrificed under light anaesthesia and brains were rapidly removed and homogenized in 8 vol. of ice-cold 0.32 M sucrose buffer containing 0.1 M EDTA, pH 7.4. The crude homogenate was centrifuged at 2220 rpm for 10 min and the supernatant recovered. The pellet was homogenized and centrifuged again and the two supernatants were pooled and centrifuged at 9250 rpm for 10 min, +4° C. The pellet was resuspended in fresh buffer and centrifuged at 11250 rpm for 10 min, +4° C. The resulting pellet was stored at −80° C. until use.

In vitro enzyme activities assay: the enzyme activities were assessed with a radioenzymatic assay using the selective substrates $^{14}$C-serotonin (5-HT) and $^{14}$C-phenylethylamine (PEA) for MAO-A and MAO-B, respectively.

The mitochondrial pellet (500 μg protein) was resuspended in 0.1 M phosphate buffer pH 7.4 and 500 μl was added to 50 μl of the test compound or buffer for 30 min at 37° C. (pre-incubation) then the substrate (50 μl) was added. The incubation was carried out for 30 min at 37° C. ($^{14}$C-5-HT, 5 μM) or for 10 min at 37° C. ($^{14}$C-PEA, 0.5 μM).

The reaction was stopped by adding 0.2 ml HCl or perchloric acid. After centrifugation, the deaminated metabolites were extracted with 3 ml of diethylether (5-HT) or toluene (PEA) and the radioactive organic phase measured by liquid scintillation spectrometry at 90% efficiency. Radioactivity in the eluate indicates the production of neutral and acidic metabolites formed as a result of MAO activity.

The enzymatic activity was expressed as nmoles of substrate transformed/mg protein/min. The activity of MAO in the sample was expressed as a percentage of control activity in the absence of inhibitors after subtraction of appropriate blank values.

The drug inhibition curves were obtained from at least eight different concentrations, each in duplicate ($10^{-10}$ to $10^{-5}$ M) and the IC$_{50}$ values (the drug concentration inhibiting 50% enzyme activity) with confidence intervals determined using non linear regression analysis (best fitting aided-computer program).

EXAMPLE 5

In Vitro MAO-B Inhibition Reversibility Studies

To investigate whether the test compound was an irreversible or a reversible MAO-B inhibitor, the inhibition of the enzymatic activity was assessed using two experimental protocols:

a) Time-Dependent Experiments:

the time-dependent association kinetics were measured as the IC$_{50}$ values after 0 or 30 min enzyme-inhibitor incubation. For mechanism-based irreversible inhibitors that act by blocking the enzyme catalytic site, the inhibitory potency increases with incubation time. The absence of significant difference between IC$_{50}$ with or without preincubation is indicative for reversible inhibitors.

b) Washing Experiments:

rat brain mitochondria (enzyme) and test compound (inhibitor) were preincubated for 30 min at 37° C. before being subjected to repeated centrifugations and resuspensions. MAO-B activity was assessed immediately and after each centrifugation resuspension cycles (1-5). Percentage inhibition was calculated with respect to samples treated in the same manner but in the absence of inhibitor.

The recovery of MAO-B activity after washings of the enzyme-test compound complex is indicative for reversible inhibitors.

EXAMPLE 6

Ex Vivo MAO-B Inhibition

Test compounds were administered orally to male C57BL mice (Harlan, Italy, 25-27 g) at the single dose of 20 mg/Kg. At different time intervals (1, 2, 4, 8 and 24 h), animals were sacrificed, brains removed, cortices dissected out and stored at −80° C. Crude homogenates (0.5%) were prepared in 0.1 M phosphate buffer pH 7.4 and freshly used. MAO-A and MAO-B activity were assessed as above described.

EXAMPLE 7

In Vitro Binding of $^3$H-Batrachotoxin in Rat Brain Membranes

Membrane preparations (P2 fraction) Male Wistar rats (Harlan, Italy—175-200 g) were sacrificed under light anaesthesia and brains were rapidly removed and cortex was dissected out, homogenized in 10 vol. of ice-cold 0.25 M sucrose buffer (50 mM Tris.HCl, pH 7.4). The crude homogenate was centrifuged at 3250 rpm for 10 min and the supernatant recovered. The pellet was homogenized and centrifuged again and the two supernatants were pooled and centrifuged at 14750 rpm for 10 min, +4° C. The resulting pellet was stored at −20° C. until use.

Binding assay. The pellet was resuspended in 50 mM Hepes buffer, pH 7.4 containing 0.8 mM MgSO$_4$, 5.4 mM KCl, 5.5 mM glucose and 130 mM choline using Polytron PT10. The binding assay was carried out in 0.25 ml final volume containing 50 μl of membrane preparation (ca 200 μg of protein), 50 μl of $^3$H-batrachotoxin ligand (10 nM), 50 μl of TTX (1 μM), 50 μl of scorpion toxin (37.5 μg/ml) and 50 μl of test compound or buffer or 300 μM of veratridine to determine non specific binding. The binding assay was performed at 37° C. for 30 min and stopped by rapid filtration under vacuum through Whatman GF/B glass fiber filters. Filters (pre-soaked with polyethylenimine 0.1%) were washed with 3×5 ml of ice-cold buffer and placed in picovials containing scintillation cocktail (Filter Count, Packard). Radioactivity bound was measured by liquid scintillation spectrometry at 45% efficiency.

Data analysis. The IC$_{50}$ was calculated from displacement curves by computer program LIGAND (McPherson, J. Pharmacol. Methods, 14, 213. 1985). The displacement curves were obtained using at least 9 concentrations, each in duplicate, covering a 100000 fold range.

EXAMPLE 8

In Vitro Binding of $^3$H-Nitrendipine in Rat Brain Membranes

Membrane preparations Male Wistar rats (Harlan, Italy—175-200 g) were sacrificed under light anaesthesia and brains were rapidly removed and cortex was dissected out, homogenized in 10 vol. of ice-cold 50 mM Tris.HCl, pH 7.7 using Polytron PT10. The crude homogenate was centrifuged at 50000×g for 10 min. The pellet was homogenized and centrifuged twice in fresh buffer at 50000×g for 10 min, +4° C. The resulting pellet was stored at −20° C. until use.

Binding assay. The pellet was resuspended in 50 mM Tris HCl, pH 7.7 using Polytron PT10. The binding assay was carried out in 1 ml final volume containing 900 μl of membrane preparation (ca 700 μg of protein), 50 μl of 3H-nitrendipine (0.15 nM), and 50 μl of test compound or buffer or 1 μM of nifedipine to determine non specific binding. The binding assay was performed at 25° C. for 45 min and stopped by rapid filtration under vacuum through Whatman GF/B glass fiber filters. Filters were washed with 3×5 ml of ice-cold buffer and placed in picovials containing scintillation cocktail (Filter Count, Packard). Radioactivity bound was measured by liquid scintillation spectrometry at 45% efficiency.

Data analysis. The IC$_{50}$ was calculated from displacement curves by computer program LIGAND (McPherson, J. Pharmacol. Methods, 14, 213. 1985). The displacement curves were obtained using at least 9 concentrations, each in duplicate, covering a 100000 fold range.

EXAMPLE 9

Calcium Influx Assay

IMR32 human neuroblastoma cells constitutively possess both L and N type channels. Under differentiating conditions, IMR32 preferentially express on the membrane surface N-type calcium channels. The remaining L-type calcium channels were blocked using the selective L type blocker, nifedipine. In these experimental conditions, only N type channels can be detected.

IMR32 cells were differentiated using 1 mM dibutyrril-cAMP and 2.5 µM bromodeoxyuridine for 8 days (4 times) in 225 cm² flask, then detached, seeded at 200,000 cells/well on 96 polylysine-coated plates and further incubated for 18-24 h in the presence of differentiating buffer before use.

The $Ca^{2+}$ Kit Assay (Molecular Devices), based on a fluorescent calcium indicator 485-535 nm wavelength, was used.

Differentiated cells were incubated with dye loading for 30 min at 37° C. then, nifedipine alone (1 µM) or in the presence of ω-conotoxin or test compounds were added for further 15 min.

The fluorescence (485-535 nm) was measured before and after (30-40 sec) the automated injection of 100 mM KCl depolarizing solution using a Victor plate reader (Perkin Elmer).

The inhibition curves were calculated from 5 concentrations, each in triplicate, and the $IC_{50}$ determined using a linear regression analysis.

Preferred compounds of general formula 1 inhibit N-type calcium channels with an $IC_{50}$ value less than 10 µM.

EXAMPLE 10

Electrophysiological Assay

Experiments for the determination of the tonic block are carried out on isolated *Xenopus* oocytes expressing the Na channel Nav 1.3. Currents are recorded using the two electrodes voltage clamp (TEVC) technique Oocytes Preparation:

The frog (*Xenopus Laevis*) is anesthesized in a solution with 3-aminobenzoic acid ethyl ester (1 µl) and, after 25 minutes, it is placed on its back on an "iced-bed". The skin and the others tissues are cut, the ovarian lobes are pulled out and kept in ND96ØCa²⁺ (NaCl 96 mM, KCl 2 mM, MgCl2 1 mM, Hepes 10 mM, pH 7.85 with NaOH)

After the removal of the oocytes, the muscle and the skin are sutured separately.

Ovarian lobes are reduced into clusters of 10/20 oocytes, put in tubes with collagenase solution (1 mg/ml) and kept in movement for about 1 h in an incubator.

At the end of this step, when the oocytes are well separated ones from the others, they are rinsed three times with ND96ØCa²⁺ and three times with NDE (ND96ØCa²⁺+CaCl 0.9 mM, MgCl2 0.9 mM, piruvate 2.5 mM, gentamicine 50 mg/l).

The oocytes obtained are at different stages of development. Only cells at stages V or VI are selected for RNA injection subsequent experiments.

The day after the preparation, the oocytes are injected (Drummond Nanoject) with 20 ng Nav1.3 cRNA and maintained in NDE.

Starting from 48 h after the mRNA injection whole cell currents are recorded using a two-microelectrode voltage clamp automated workstation.

Typical Microelectrodes have a resistance of 0.5 to 1 Mohm and are filled with KCl 3M.

Control bath solution containes (mM): NaCl 98, $MgCl_2$ 1, $CaCl_2$ 1.8, HEPES 5 (pH 7.6).

Compounds are prepared in stock solutions (20 mM) and dissolved to the final concentrations in the external bath solution.

Currents Recording:

The current/voltage (I/V) relationship for the Nav1.3 currents expressed in oocytes was first studied in order to determine the membrane potential evoking the maximal activation. Nav1.3 showed the max activation at 0 mV, that we used as test potential (Vtest) for tonic block studies.

The steady—state inactivation properties of the Nav1.3 currents were than studied in order to determine the membrane potentials for the resting state (Vrest) at which channel availability is maximal (Imax), and the membrane potential for the half maximal inactivation (V ½) producing half of the max current availability (I ½) respectively. This two voltage conditions were then used for the evaluation of the voltage dependence of the tonic block.

Finally a two-step protocol was used to determine the voltage dependence of the block of Nav1.3: the oocytes were clamped at −80 mV, the currents were activated by a 100 ms step pulse to 0 mV (Vtest) from a 3000 ms preconditioning potential at −80 mV (resting, Imax condition) and −40 mV (depolarized, I ½ condition), respectively.

Current amplitudes in the two conditions were recorded in the absence and in the presence of different concentrations of compound (washout was made in between) in order to determine the concentration—inhibition curves and $IC_{50}$ values for the tonic block in the depolarized (half max current availability) conditions.

Preferred compounds of general formula 1 inhibit Nav 1.3 sodium channels with an $IC_{50}$ value lower than the reference sodium channel blocker ralfinamide.

EXAMPLE 11

Maximal Electroshock Test in Rats and Mice

Wistar rats received an electroshock (160 mA for 0.2 s with a pulse train of 60 Hz having a pulse duration of 0.4 ms; ECT unit model 7801, Ugo Basile, Comerio, Italy) through intra-aural clip electrodes sufficient to produce a hindlimb tonic extensor response in at least 97% of control animals.

Mice received a 28 mA shock of 0.7 s with a pulse train of 80 Hz having a pulse duration of 0.4 ms. Several doses of the test compound and standard AEDs were administered to groups of 10 to 20 mice or rats per dose in a volume of 5 ml/kg 60 min p.o. or 30 min i.p. before induction of MES to calculate $ED_{50}$ values. The complete suppression of the hindlimb tonic extensor component of seizures was taken as evidence of anticonvulsant activity.

EXAMPLE 12

Mice Formalin Test

According to a modified protocol from Rosland et al., (1990) mice were injected subcutaneously (s.c.) with 20 µl of 2.7% solution of formalin into the plantar surface of left hindpaw and placed immediately into clear PVC observation chambers (23×12×13 cm). Pain behaviour was quantified by counting the cumulative licking time (s) of the injected paw. Measurements were taken during the early phase (0-5 min) and late phase (30-40 min) after formalin injection (Tjolsen et al. 1992).

The test compound was administered p.o. 15 min before formalin injection in a volume of 10 ml/kg body weight to groups of 10 mice per dose. Control group was treated with vehicle.

EXAMPLE 13

Carragenan Model of Inflammation

Male Wistar rats of 175-200 grams were used.
The left hind paw was injected with 100 μl of carrageenan (2% w/v in saline). Compounds of the invention (30 mg/kg), indomethacin (5 mg/kg) or control vehicle (such as distilled water) were orally administered 1 h before carrageenan injection. The paw volume was measured with a plethysmometer (Ugo Basile) immediately before (basal) and 1, 2, 3, 4 and 5 h after the carrageenan injection.

The invention claimed is:
1. A compound according to formula I:

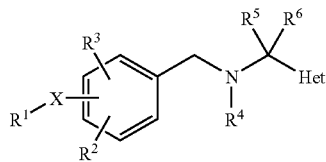

I wherein,
X is oxygen, sulphur or a $NR^7$ group;
$R^1$ is $C_3$-$C_8$ alkyl or $C_1$-$C_8$ alkyl substituted by phenoxy or phenyl, both phenoxy or phenyl being optionally substituted by one or more fluoro, chloro, trifluotomethyl, $C_1$-$C_6$ alkyl, hydroxyl, or $C_1$-$C_6$ alkoxy;
$R^2$ and $R^3$ are independently hydrogen, $C_1$-$C_6$ alkyl, halogen, trifluoromethyl, hydroxy or $C_1$-$C_6$ alkoxy;
$R^4$ is hydrogen or $C_1$-$C_8$ alkyl;
$R^5$ and $R^6$ are independently hydrogen or $C_1$-$C_3$ alkyl, optionally substituted by hydroxy or phenyl;
$R^7$ is hydrogen or straight or branched $C_1$-$C_3$ alkyl;
Het is a five to seven membered, saturated or unsaturated, heteromonocyclic or an eight to ten membered, saturated or unsaturated, heterobicyclic group, containing one or more heteroatoms chosen independently from nitrogen, oxygen and sulphur, said monocyclic or bicyclic groups being optionally substituted by $C_1$-$C_6$ alkyl, halogen, hydroxyl or $C_1$-$C_6$ alkoxy; or
the pharmaceutically acceptable salt thereof,
with the proviso that:
Het cannot be indole, benzo[b]furan, benzo[b]thiophen, chroman, when $R^5$ and $R^6$ are both hydrogen, or Het cannot be 2-pyridyl;
when $R^1$ is unsubstituted or substituted benzyl, and $R^2$ and $R^3$ are hydrogen, halogen or alkoxy, $R^4$ is other than hydrogen;
when $R^1$ is propyl or butyl, $R^2$, $R^3$, $R^5$ and $R^6$ are hydrogen and $R^4$ is hydrogen, methyl or ethyl, Het cannot be 1,4-benzodioxan;
when X—$R^1$ is a para butyloxy group and $R^2$, $R^3$, $R^4$, $R^5$ and $R^6$ are hydrogen, Het cannot be 2-thiophenyl, or 4-(2,2'-dimethyl)-pyranyl;
when X—$R^1$ is an ortho heptyloxy or octyloxy group and $R^2$, $R^3$, $R^4$, $R^5$ and $R^6$ are hydrogen, Het cannot be 2-furyl; and
when X—$R^1$ is an ortho O—$(CH_2)_m$-p-$CF_3$-phenyl group, where m is an integer from 1 to 3, and $R^2$, $R^3$, $R^5$ and $R^6$ are hydrogen, Het cannot be pyridyl.

2. A medicament having sodium and/or calcium channel modulating activity and/or selective MAO-B inhibiting activity, said medicament comprising:
a compound according to formula I:

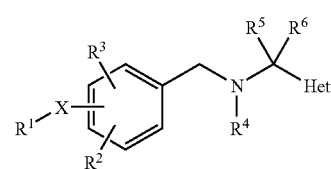

I wherein,
$R^1$ is $C_3$-$C_8$ alkyl or $C_1$-$C_8$ alkyl substituted by phenoxy or phenyl, both phenoxy or phenyl being optionally substituted by one or more fluoro, chloro, trifluotomethyl, $C_1$-$C_6$ alkyl, hydroxyl, or $C_1$-$C_6$ alkoxy,
$R^2$ and $R^3$ are independently hydrogen, $C_1$-$C_6$ alkyl, halogen, trifluoromethyl, hydroxy or $C_1$-$C_6$ alkoxy,
$R^4$ is hydrogen or $C_1$-$C_8$ alkyl,
$R^5$ and $R^6$ are independently hydrogen or $C_1$-$C_3$ alkyl, optionally substituted by hydroxy or phenyl,
$R^7$ is hydrogen or straight or branched $C_1$-$C_3$ alkyl,
Het is a five to seven membered, saturated or unsaturated, heteromonocyclic or an eight to ten membered, saturated or unsaturated, heterobicyclic group, containing one or more heteroatoms chosen independently from nitrogen, oxygen and sulphur, said monocyclic or bicyclic groups being optionally substituted by $C_1$-$C_6$ alkyl, halogen, hydroxyl or $C_1$-$C_6$ alkoxy, or
the pharmaceutically acceptable salts thereof,
with the proviso that:
Het cannot be an indole, chroman when $R^5$ and $R^6$ are both hydrogen,
when X—$R^1$ is an ortho O—$(CH_2)_m$-p-$CF_3$-phenyl group, where m is an integer from 1 to 3, and $R^2$, $R^3$, $R^5$ and $R^6$ are hydrogen, Het cannot be pyridyl or the pharmaceutically acceptable salts or prodrug thereof.

3. The medicament according to claim 2, wherein for the compound according to formula I:
$R^1$ is benzyl or $C_5$-$C_8$ alkyl,
$R^4$, $R^5$ and $R^6$ are hydrogen or $C_1$-$C_3$ alkyl,
X is oxygen, and
Het is furan, tetrahydrofuran, isoxazol, oxazol, thiophen, pyran, or dioxane, unsubstituted or substituted by $C_1$-$C_3$ alkyl.

4. The medicament according to claim 2, wherein the compound according to formula I is selected from the group consisting of:
(4-Pentyloxy-benzyl)-(furan-2-ylmethyl)-amine;
(4-Heptyloxy-benzyl)-(furan-2-ylmethyl)-amine;
(R)(4-Pentyloxy-benzyl)-(tetrahydro-furan-2-ylmethyl)-amine;
(S)(4-Pentyloxy-benzyl)-(tetrahydro-furan-2-ylmethyl)-amine;
(R)(4-Heptyloxy-benzyl)-(tetrahydro-furan-2-ylmethyl)-amine;

(S)(4-Heptyloxy-benzyl)-(tetrahydro-furan-2-ylmethyl)-amine;
(R)(4-Pentyloxy-benzyl)-(tetrahydro-pyran-2-ylmethyl)-amine;
(S)(4-Pentyloxy-benzyl)-(tetrahydro-pyran-2-ylmethyl)-amine;
(R)(4-Heptyloxy-benzyl)-(tetrahydro-pyran-2-ylmethyl)-amine;
(S)(4-Heptyloxy-benzyl)-(tetrahydro-pyran-2-ylmethyl)-amine;
(4-Benzyloxy-benzyl)-(furan-2-ylmethyl)-amine;
(4-Benzyloxy-benzyl)-(5-methyl-furan-2-ylmethyl)-amine;
[4-(3-Fluoro-benzyloxy)-benzyl]-(furan-2-ylmethyl)-amine;
[4-(3-Chloro-benzyloxy)-benzyl]-(furan-2-ylmethyl)-amine;
[4-(3-Fluoro-benzyloxy)-benzyl]-(5-methyl-furan-2-ylmethyl)-amine;
[4-(3-Chloro-benzyloxy)-benzyl]-(5-methyl-furan-2-ylmethyl)-amine;
(R)(4-Benzyloxy-benzyl)-[1-(furan-2-yl)-1-ethyl]-amine;
(S)(4-Benzyloxy-benzyl)-[1-(furan-2-yl)-1-ethyl]-amine;
[4-(3-Fluoro-benzyloxy)-benzyl]-[1-(furan-2-yl)-1-ethyl]-amine;
[4-(3-Chloro-benzyloxy)-benzyl]-[1-(furan-2-yl)-1-ethyl]-amine;
(R)(4-Benzyloxy-benzyl)-(tetrahydro-furan-2-ylmethyl)-amine;
(S)(4-Benzyloxy-benzyl)-(tetrahydro-furan-2-ylmethyl)-amine;
(R)[4-(3-Fluoro-benzyloxy)-benzyl]-(tetrahydro-furan-2-ylmethyl)-amine;
(S)[4-(3-Fluoro-benzyloxy)-benzyl]-(tetrahydro-furan-2-ylmethyl)-amine;
(R)[4-(3-Chloro-benzyloxy)-benzyl]-(tetrahydro-furan-2-ylmethyl)-amine;
(S)[4-(3-Chloro-benzyloxy)-benzyl]-(tetrahydro-furan-2-ylmethyl)-amine;
(R)[4-(3-Fluoro-benzyloxy)-benzyl]-(tetrahydro-pyran-2-ylmethyl)-amine;
(S)[4(3-Fluoro-benzyloxy)-benzyl]-(tetrahydro-pyran-2-ylmethyl)-amine;
(R)[4-(3-Chloro-benzyloxy)-benzyl]-(tetrahydro-pyran-2-ylmethyl)-amine;
(S)[4-(3-Chloro-benzyloxy)-benzyl]-(tetrahydro-pyran-2-ylmethyl)-amine;
(4-Benzyloxy-benzyl)-(1,4-dioxan-2-ylmethyl)-amine;
[4-(3-Chloro-benzyloxy)-benzyl]-(pyrido-2-ylmethyl)-amine;
[4-(3-Chloro-benzyloxy)-benzyl]-(pyrido-3-ylmethyl)-amine;
[4-(3-Chloro-benzyloxy)-benzyl]-(pyrido-4-ylmethyl)-amine;
[4-(3-Chloro-benzyloxy)-benzyl]-(imidazol-2-ylmethyl)-amine;
[4-(3-Chloro-benzyloxy)-benzyl]-(1-methyl-imidazol-2-ylmethyl)-amine;
[4-(3-Chloro-benzyloxy)-benzyl]-(5-methyl-1H-triazol-2-ylmethyl)-amine;
[4-(3-Chloro-benzyloxy)-benzyl]-(4-methyl-thiazol-2-ylmethyl)-amine;
(4-Benzyloxy-benzyl)-(isoxazol-5-ylmethyl)-amine;
[4-(3-Fluoro-benzyloxy)-benzyl]-(isoxazol-5-ylmethyl)-amine;
[4-(3-Chloro-benzyloxy)-benzyl]-(isoxazol-5-ylmethyl)-amine;
(4-Benzyloxy-benzyl)-(3-methyl-isoxazol-5-ylmethyl)-amine;
[4-(3-Fluoro-benzyloxy)-benzyl]-(3-methyl-isoxazol-5-ylmethyl)-amine;
[4-(3-Chloro-benzyloxy)-benzyl]-(3-methyl-isoxazol-5-ylmethyl)-amine;
(4-Benzyloxy-benzyl)-(oxazol-2-ylmethyl)-amine;
[4-(3-Fluoro-benzyloxy)-benzyl]-(oxazol-2-ylmethyl)-amine;
[4-(3-Chloro-benzyloxy)-benzyl]-(oxazol-2-ylmethyl)-amine;
(4-Benzyloxy-benzyl)-(oxazol-5-ylmethyl)-amine;
[4-(3-Fluoro-benzyloxy)-benzyl]-(oxazol-5-ylmethyl)-amine;
[4-(3-Chloro-benzyloxy)-benzyl]-(oxazol-5-ylmethyl)-amine;
(4-Benzyloxy-benzyl)-(thiophen-2-ylmethyl)-amine;
[2-(3-Chloro-benzyloxy)-benzyl]-(thiophen-2-ylmethyl)-amine;
[2-(3-Fluoro-benzyloxy)-benzyl]-(thiophen-2-ylmethyl)-amine;
[3-(3-Chloro-benzyloxy)-benzyl]-(thiophen-2-ylmethyl)-amine;
[3-(3-Fluoro-benzyloxy)-benzyl]-(thiophen-2-ylmethyl)-amine;
[4-(3-Chloro-benzyloxy)-benzyl]-(thiophen-2-ylmethyl)-amine;
[4-(3-Fluoro-benzyloxy)-benzyl]-(thiophen-2-ylmethyl)-amine;
[2-(3-Fluoro-benzyloxy)-benzyl]-(benzo[b]furan-2-ylmethyl)-amine;
[3-(3-Fluoro-benzyloxy)-benzyl]-(benzo[b]furan-2-ylmethyl)-amine;
[4-(3-Fluoro-benzyloxy)-benzyl]-(benzo[b]furan-2-ylmethyl)-amine;
(R)[4-(3-Fluoro-benzyloxy)-benzyl]-(dihydro-benzo[b]furan-2-ylmethyl)-amine;
(S)[4-(3-Fluoro-benzyloxy)-benzyl]-(dihydro-benzo[b]furan-2-ylmethyl)-amine:
[4-(3-Chloro-benzyloxy)-benzyl]-(benzimidazol-2-ylmethyl)-amine;
either as a single isomer or as a mixture of isomers thereof, or the pharmaceutically acceptable salt thereof.

5. A process for the preparation of a compound of formula I according to claim 1, or a pharmaceutically acceptable salt thereof, the process comprising:

a) reacting a compound of formula II

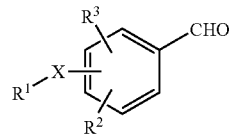

wherein
X is oxygen, sulphur or a $NR^7$ group,
$R^1$ is $C_3$-$C_8$ alkyl or $C_1$-$C_8$ alkyl substituted by phenoxy or phenyl, both phenoxy or phenyl being optionally substituted by one or more fluoro, chloro, trifluotomethyl, $C_1$-$C_6$ alkyl, hydroxyl, or $C_1$-$C_6$ alkoxy,
$R^2$ and $R^3$ are independently hydrogen, $C_1$-$C_6$ alkyl, halogen, trifluoromethyl, hydroxy or $C_1$-$C_6$ alkoxy,
with a compound of formula III

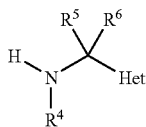

wherein
- $R^4$ is hydrogen or $C_1$-$C_8$ alkyl,
- $R^5$ and $R^6$ are independently hydrogen or $C_1$-$C_3$ alkyl, optionally substituted by hydroxy or phenyl,
- $R^7$ is hydrogen or straight or branched $C_1$-$C_3$ alkyl,
- Het is a five to seven membered, saturated or unsaturated, heteromonocyclic or an eight to ten membered, saturated or unsaturated, heterobicyclic group, containing one or more heteroatoms chosen independently from nitrogen, oxygen and sulphur, said monocyclic or bicyclic groups being optionally substituted by $C_1$-$C_6$ alkyl, halogen, hydroxyl or $C_1$-$C_6$ alkoxy, with the proviso that:

Het cannot be indole, benzo[b]furan, benzo[b]thiophen, chroman, when $R^5$ and $R^6$ are both hydrogen, or Het cannot be 2-pyridyl, when $R^1$ is unsubstituted or substituted benzyl, and $R^2$ and $R^3$ are hydrogen, halogen or alkoxy, $R^4$ is other than hydrogen, when $R^1$ is propyl or butyl, $R^2$, $R^3$, $R^5$ and $R^6$ are hydrogen and $R^4$ is hydrogen, methyl or ethyl, Het cannot be 1,4-benzodioxan, when X—$R^1$ is a para butyloxy group and $R^2$, $R^3$, $R^4$, $R^5$ and $R^6$ are hydrogen, Het cannot be 2-thiophenyl, or 4-(2,2'-dimethyl)-pyranyl, when X—$R^1$ is an ortho heptyloxy or octyloxy group and $R^2$, $R^3$, $R^4$, $R^5$ and $R^6$ are hydrogen, Het cannot be 2-furyl, and when X—$R^1$ is an ortho O—$(CH_2)_m$-p-$CF_3$-phenyl group, where m is an integer from 1 to 3, and $R^2$, $R^3$, $R^5$ and $R^6$ are hydrogen, Het cannot be pyridyl, in the presence of a reducing agent, or b) reacting a compound of formula III as defined above with a compound of formula IV,

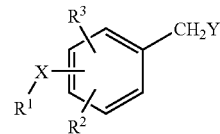

wherein
- X is oxygen, sulphur or a $NR^7$ group,
- $R^1$ is $C_3$-$C_8$ alkyl or $C_1$-$C_8$ alkyl substituted by phenoxy or phenyl, both phenoxy or phenyl being optionally substituted by one or more fluoro, chloro, trifluotomethyl, $C_1$-$C_6$ alkyl, hydroxyl, or $C_1$-$C_6$ alkoxy,
- $R^2$ and $R^3$ are independently hydrogen, $C_1$-$C_6$ alkyl, halogen, trifluoromethyl, hydroxy or $C_1$-$C_6$ alkoxy,
- Y is a halogen atom or a O-EWG group, where the EWG means an electron withdrawing group, able to transform the oxygen to which the group is linked, into a leaving group and, optionally, converting a compound of the invention into another compound of the invention and/or, optionally, converting the compound of formula IV into a pharmaceutically acceptable salt and/or, optionally, converting a salt into a free compound.

6. A pharmaceutical composition comprising:
the compound according to claim 1, as an active principle, or a pharmaceutically acceptable salt thereof; and
a suitable carrier and/or diluent and optionally other therapeutic agents.

* * * * *

UNITED STATES PATENT AND TRADEMARK OFFICE
CERTIFICATE OF CORRECTION

PATENT NO. : 7,649,005 B2  Page 1 of 1
APPLICATION NO. : 10/575627
DATED : January 19, 2010
INVENTOR(S) : Salvati et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 749 days.

Signed and Sealed this

Twenty-eighth Day of December, 2010

David J. Kappos
*Director of the United States Patent and Trademark Office*